US012558176B2

(12) United States Patent     (10) Patent No.:   US 12,558,176 B2
Lynch et al.     (45) Date of Patent:    Feb. 24, 2026

(54) CONTROLLED RESISTANCE IN BACKDRIVABLE JOINTS

(71) Applicant: Intuitive Surgical Operations, Inc., Sunnyvale, CA (US)

(72) Inventors: Goran Lynch, Sunnyvale, CA (US); Sean Duffy, Sunnyvale, CA (US); Will Valladao, Sunnyvale, CA (US); Amin Zeiaee, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 202 days.

(21) Appl. No.: 18/286,623

(22) PCT Filed: Apr. 11, 2022

(86) PCT No.: PCT/US2022/024284
§ 371 (c)(1),
(2) Date: Oct. 12, 2023

(87) PCT Pub. No.: WO2022/221204
PCT Pub. Date: Oct. 20, 2022

(65) Prior Publication Data

US 2024/0189051 A1     Jun. 13, 2024

Related U.S. Application Data

(60) Provisional application No. 63/174,028, filed on Apr. 12, 2021.

(51) Int. Cl.
A61B 34/37       (2016.01)
A61B 34/30       (2016.01)
(Continued)

(52) U.S. Cl.
CPC .............. A61B 34/37 (2016.02); A61B 34/35 (2016.02); A61B 2034/302 (2016.02)

(58) Field of Classification Search
CPC ... A61B 34/37; A61B 34/35; A61B 2034/302; A61B 34/30; G05B 19/423; B25J 9/1689; B25J 9/1656
(Continued)

(56) References Cited

U.S. PATENT DOCUMENTS 5,568,029 A * 10/1996 Chan ...................... G05B 19/19
                                                 318/644
6,587,750 B2 * 7/2003 Gerbi ..................... A61B 34/70
                                                 600/595
(Continued)

FOREIGN PATENT DOCUMENTS

EP          2135637 B1     5/2014
EP          2263595 B1     9/2014
(Continued)

OTHER PUBLICATIONS

Choi I., et al., "Hybrid Actuation With Unidirectional Clutches for Handheld Haptic Controllers," IEEE Robotics and Automation Letters, IEEE, Jul. 2021, vol. 6 (3), pp. 4827-4834.
(Continued)

*Primary Examiner* — Jaime Figueroa
(74) *Attorney, Agent, or Firm* — Osha Bergman Watanabe & Burton LLP

(57)             ABSTRACT

A computer-assisted system includes a manipulator arm including a joint, an actuator mechanism configured to drive the joint, and a controller including a computer processor. The controller is communicatively coupled to the manipulator arm and configured with a first control mode and a second control mode. In each of the first control mode and the second control mode, the controller commands the actuator mechanism to allow an external articulation to reconfigure the manipulator arm by backdriving the joint. The first control mode is distinguished from the second control mode at least by the controller being configured to, (Continued)

in the first control mode, command the actuator mechanism to provide a first speed-dependent resistance in response to the joint being backdriven at a first backdriven speed above a first speed threshold. The first speed-dependent resistance opposes the joint being backdriven.

20 Claims, 10 Drawing Sheets

(51) Int. Cl.
　　　*A61B 34/35*　　　(2016.01)
　　　*B25J 9/16*　　　(2006.01)
(58) Field of Classification Search
　　　USPC ................. 700/245–264; 318/568.11–568.25
　　　See application file for complete search history.

(56)　　　　　　　References Cited

U.S. PATENT DOCUMENTS

| | | | | |
|---|---|---|---|---|
| 6,786,896 | B1 * | 9/2004 | Madhani | A61B 34/30 |
| | | | | 606/1 |
| 7,087,049 | B2 | 8/2006 | Nowlin et al. | |
| 8,004,229 | B2 | 8/2011 | Nowlin et al. | |
| 8,123,740 | B2 * | 2/2012 | Madhani | A61B 34/70 |
| | | | | 606/1 |
| 8,541,970 | B2 | 9/2013 | Nowlin et al. | |
| 8,624,537 | B2 | 1/2014 | Nowlin et al. | |
| 8,749,189 | B2 | 6/2014 | Nowlin et al. | |
| 8,749,190 | B2 | 6/2014 | Nowlin et al. | |
| 8,786,241 | B2 | 7/2014 | Nowlin et al. | |
| 8,816,628 | B2 | 8/2014 | Nowlin et al. | |
| 8,823,308 | B2 | 9/2014 | Nowlin et al. | |
| 9,259,281 | B2 | 2/2016 | Griffiths et al. | |
| 9,415,510 | B2 | 8/2016 | Hourtash et al. | |
| 9,452,020 | B2 | 9/2016 | Griffiths et al. | |
| 9,820,818 | B2 * | 11/2017 | Malackowski | A61B 34/20 |
| 10,285,764 | B2 | 5/2019 | Griffiths et al. | |
| 11,166,770 | B2 * | 11/2021 | DiMaio | A61B 90/03 |
| 11,266,475 | B2 * | 3/2022 | Gomez | A61B 34/20 |
| 2005/0043718 | A1 * | 2/2005 | Madhani | A61B 34/76 |
| | | | | 606/1 |
| 2007/0013336 | A1 * | 1/2007 | Nowlin | A61B 34/30 |
| | | | | 318/568.21 |
| 2009/0012534 | A1 * | 1/2009 | Madhani | B25J 9/1689 |
| | | | | 606/130 |
| 2009/0030429 | A1 * | 1/2009 | Madhani | A61B 34/71 |
| | | | | 606/130 |
| 2010/0101346 | A1 * | 4/2010 | Johnson | F16D 7/028 |
| | | | | 901/46 |
| 2012/0143212 | A1 * | 6/2012 | Madhani | A61B 34/71 |
| | | | | 606/130 |
| 2014/0052153 | A1 * | 2/2014 | Griffiths | A61B 34/30 |
| | | | | 606/130 |
| 2014/0107666 | A1 * | 4/2014 | Madhani | A61B 34/77 |
| | | | | 901/29 |
| 2014/0188129 | A1 * | 7/2014 | Kang | A61G 13/0063 |
| | | | | 606/130 |
| 2014/0276952 | A1 * | 9/2014 | Hourtash | A61B 34/37 |
| | | | | 700/263 |
| 2014/0276953 | A1 * | 9/2014 | Swarup | A61B 50/13 |
| | | | | 606/130 |
| 2015/0032126 | A1 | 1/2015 | Nowlin et al. | |
| 2015/0051733 | A1 | 2/2015 | Nowlin et al. | |
| 2016/0100900 | A1 * | 4/2016 | Madhani | A61B 34/71 |
| | | | | 901/10 |
| 2017/0112580 | A1 * | 4/2017 | Griffiths | F16M 13/022 |
| 2017/0128136 | A1 * | 5/2017 | Post | A61B 34/30 |
| 2017/0181801 | A1 * | 6/2017 | Griffiths | A61B 50/18 |
| 2019/0015168 | A1 | 1/2019 | Verner et al. | |
| 2019/0175286 | A1 * | 6/2019 | Zhou | A61B 17/00234 |
| 2019/0216555 | A1 * | 7/2019 | DiMaio | A61B 90/03 |
| 2019/0231460 | A1 * | 8/2019 | DiMaio | A61B 50/13 |
| 2021/0128262 | A1 * | 5/2021 | Gomez | A61B 34/74 |
| 2021/0236207 | A1 * | 8/2021 | Stanton | A61B 34/30 |

FOREIGN PATENT DOCUMENTS

| | | |
|---|---|---|
| EP | 2884933 B1 | 10/2020 |
| EP | 3402433 B1 | 3/2021 |
| WO | WO-2014028699 A1 | 2/2014 |
| WO | WO-2014028702 A1 | 2/2014 |
| WO | WO-2014146107 A1 | 9/2014 |
| WO | WO-2015127078 A1 | 8/2015 |
| WO | WO-2020028356 A1 | 2/2020 |
| WO | WO-2020205634 A1 | 10/2020 |

OTHER PUBLICATIONS

International Search Report and Written Opinion for Application No. PCT/US2022/024284, mailed Jul. 15, 2022, 18 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

International Preliminary Report on Patentability for Application No. PCT/US2022/024284, mailed Oct. 26, 2023, 11 pages.

* cited by examiner

CONTROLLED RESISTANCE IN BACKDRIVABLE JOINTS

CROSS-REFERENCE TO RELATED APPLICATIONS

This application is a National Phase Application of International Application No. PCT/US2022/024284, filed on Apr. 11, 2022. International Application No. PCT/US2022/024284 claims the benefit of priority under 35 U S.C. § 119 (e) to U.S. Provisional Patent Application Ser. No. 63/174, 028, filed on Apr. 12, 2021, which is hereby incorporated by reference herein in its entirety.

BACKGROUND

Field of Invention

The present invention generally provides improved robotic and/or medical (including surgical) devices, systems, and methods.

Overview

A system of robotic devices may be used to perform a task at a worksite. For example, robotic systems may include robotic manipulator assemblies to manipulate instruments for performing the task. The robotic manipulator assembly may include two or more links coupled together by one or more joints. The joints may be active joints that are actively moved and controlled by the system. The joints may also be passive joints that are not actively moved and controlled by the system. The joints may be revolute or prismatic joints, or may be other joints such as ball joints. The configuration of the robotic manipulator assembly may be determined by the positions and orientations of the joints, the structure of the robotic manipulator assembly, and the coupling of the links.

Robotic systems include industrial and recreational robotic systems. Robotic systems also include medical robotic systems used in procedures for diagnosis, non-surgical treatment, surgical treatment, etc. As a specific example, robotic systems include minimally invasive, robotic telesurgical systems in which a surgeon may operate on a patient from bedside or a remote location. Telesurgery refers generally to surgery performed using surgical systems where the surgeon uses some form of remote control, e.g., a servomechanism, to manipulate surgical instrument movements rather than directly holding and moving the instruments by hand. A robotic medical system usable for telesurgery or other telemedical procedures may include a remotely controllable robotic manipulator assembly. Operators may remotely control motion of the remotely controllable robotic manipulator assembly. Operators may also manually move parts of the robotic medical system into positions or orientations within its environment.

SUMMARY

In one aspect, one or more embodiments relate to a computer-assisted system comprising: a manipulator arm comprising a joint, an actuator mechanism configured to drive the joint, and a controller comprising a computer processor. The controller is communicatively coupled to the manipulator arm and configured with a first control mode and a second control mode. In each of the first control mode and the second control mode, the controller commands the actuator mechanism to allow an external articulation to reconfigure the manipulator arm by backdriving the joint. The first control mode is distinguished from the second control mode at least by the controller being configured to, in the first control mode, command the actuator mechanism to provide a first speed-dependent resistance in response to the joint being backdriven at a first backdriven speed above a first speed threshold. The first speed-dependent resistance opposing the joint being backdriven.

In one aspect, one or more embodiments relate to a method for operating a robotic system comprising a manipulator arm and a controller The manipulator arm comprises a joint and an actuator mechanism configured to drive the joint. The controller is configured with a first control mode and a second control mode. The method comprises: when the controller is in each of the first control mode and the second control mode, the controller commanding the actuator mechanism to allow an external articulation to reconfigure the manipulator arm by backdriving the joint; and when the controller is in the first control mode, the controller commanding the actuator mechanism to provide a first speed-dependent resistance in response to the joint being backdriven at a first backdriven speed above a first speed threshold. The first speed-dependent resistance opposes the joint being backdriven, and the first control mode is distinguished from the second control mode at least by the first speed-dependent resistance.

Other aspects of the invention will be apparent from the following description and the appended claims.

DETAILED DESCRIPTION

Figure 1A:
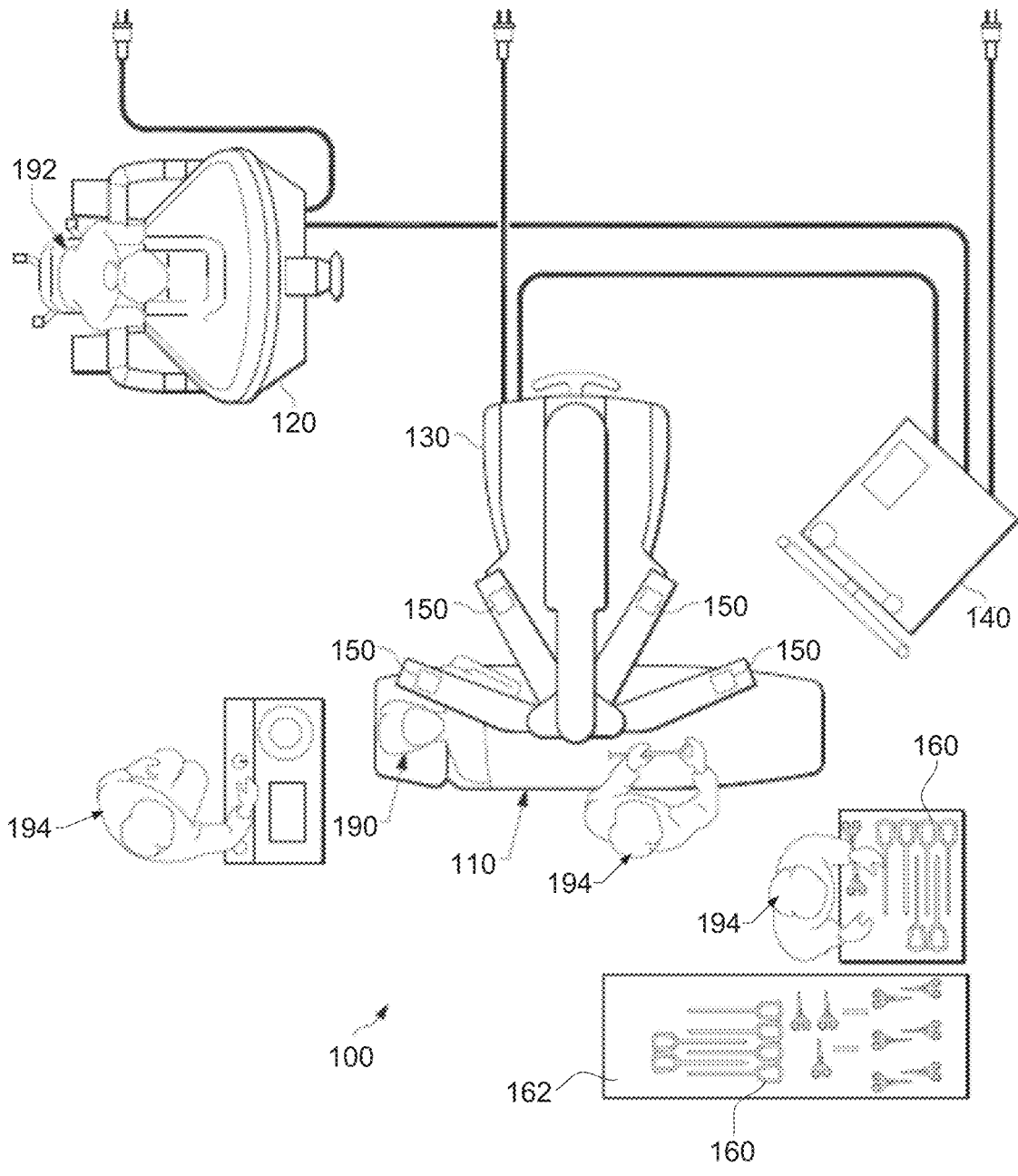
FIG. 1A shows an overhead view of a computer-assisted system in a robotic procedure scenario, in accordance with one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Although some of the examples described herein refer to surgical procedures or tools, or medical procedures and medical tools, the techniques disclosed apply to medical and non-medical procedures, and to medical and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy) and performing procedures on human or animal cadavers. Further, these techniques may also be used for medical treatment or diagnosis procedures that do, or do not, include surgical aspects.

In general, embodiments of the disclosure may facilitate the use of the robotic systems or improve the workflow under various conditions. For example, backdriving of a joint of a robotic system may be possible in multiple distinct control modes of the robotic system. It may be beneficial for a user performing the backdriving to obtain a haptic feedback enabling the identification of the current control mode. In other words, it may be desirable for the haptic feedback provided during the backdriving to be distinct for different control modes. In one or more embodiments, the haptic feedback includes a controlled resistance opposing the backdriving of the joint. The controlled resistance may be specific to the control mode. For example, in a first control mode, the controlled resistance may be higher than in a second control mode, thus enabling the user to partially or entirely differentiate the first and second control modes based on the tactile feel provided by level of resistance. Further, it may also be beneficial to provide a controlled resistance to provide tactile feedback that helps enable a user to avoid causing undesirable operating conditions of the joint. For example, in one embodiment, the controlled resistance is provided at a backdriven speed below a speed at which the actuator mechanism would saturate based on the back electromotive force (back EMF) effects of the actuator of the actuator mechanism. In such a scenario, a user backdriving the joint may perceive the controlled resistance as a signal indicating that a faster backdriving, while possible, may be undesirable. A detailed description of the controlled resistance in backdrivable joints, including possible implementations and applications is provided below.

Referring now to the drawings, in which like reference numerals represent like parts throughout the several views, FIG. 1A shows an overhead view of a computer-assisted system (100) (hereinafter system (100)) in a robotic procedure scenario. While in FIG. 1A, the computer-assisted system (100) is shown as a minimally invasive robotic surgical system, the following description is applicable to computer-assisted systems in other scenarios, e.g., non-surgical scenarios or non-medical scenarios. In the example of FIG. 1A, a diagnostic or therapeutic procedure is performed on a patient (190) who is lying on an operating table (110). The system (100) may include a user control system (120) for use by a user (192) (e.g. a clinician such as surgeon in a medical example) during the procedure. One or more assistants (194) may also participate in the procedure. The system (100) may further include a robotic manipulating system (130) (e.g., a patient-side robotic device in a medical example) and an auxiliary system (140). The robotic manipulating system (130) may include at least one manipulator arm (150), each of which may support a removably coupled tool (160) (also called instrument (160)). In the illustrated medical procedure of FIG. 1A, the tool (160) may enter the body of the patient (190) through a natural orifice such as the mouth or anus, or through an incision such as an incision in a body wall such as an abdominal wall, while the user (192) views the worksite (e.g. a surgical site in the surgical scenario) through the user control system (120). An image of the worksite may be obtained by a tool (160) comprising an imaging device (e.g. an endoscope, an optical camera, an ultrasonic probe, etc.) usable to image the worksite, which may be manipulated by the robotic manipulating system (130) so as to position and orient the imaging device. The auxiliary system (140) may be used to process the images of the worksite for display to the user (192) through the user control system (120) or other display systems located locally or remotely from the procedure. The number of tools (160) used at one time generally depends on the task and space constraints, among other factors. If it is appropriate to change, clean, inspect, or reload one or more of the tools (160) being used during a procedure, an assistant (194) may remove the tool (160) from the manipulator arm (150), and replace it with the same tool (160) or another tool (160). Tools (160) may be stored on a tray (162) or another type of tool storage.

Figure 1B:
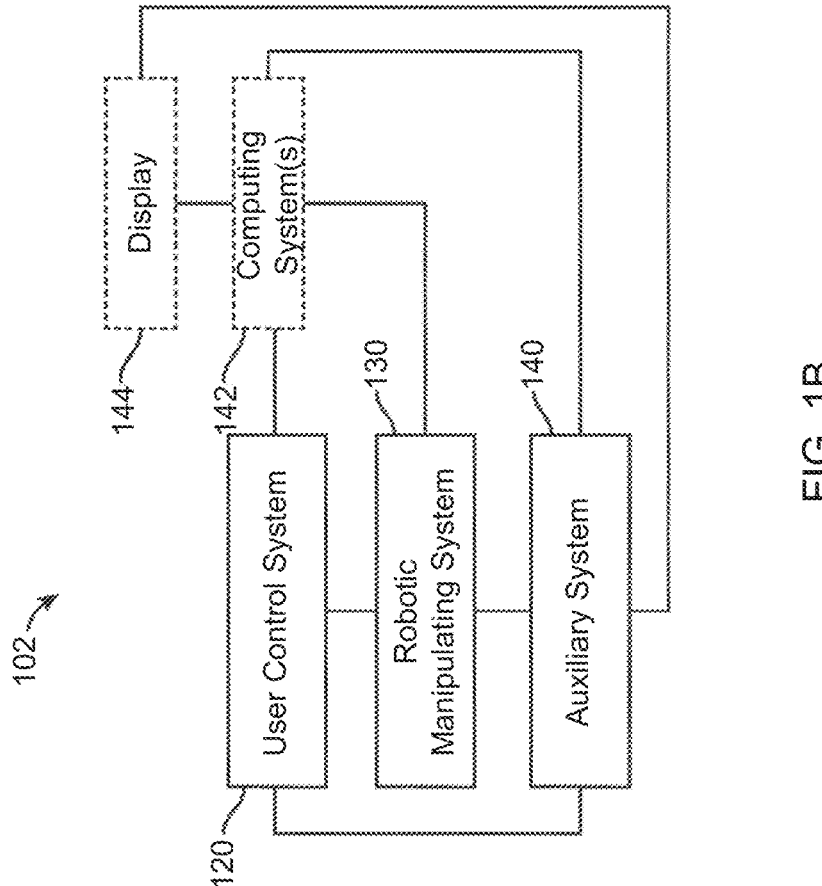
FIG. 1B diagrammatically shows various components of the computer-assisted system, such as the one of FIG. 1A, in accordance with one or more embodiments.

FIG. 1B diagrammatically shows a system (102) of a computer-assisted system (100). As noted above, the computer-assisted system (100) may be a computer-assisted medical system such as a robotic surgical system, or a non-medical system such as a computer-assisted industrial or recreational system. The system (102) may include one or more computing systems (142). A computing system (142) may be used to process input provided by the user control system (120) from a user. A computing system (142) may further be used to provide an output, e.g., a video image to the display (144). One or more computing systems (142) may further be used to control the robotic manipulating system (130).

A computing system (142) may include one or more computer processors, non-persistent storage (e.g., volatile memory, such as random access memory (RAM), cache memory), persistent storage (e.g., a hard disk, an optical drive such as a compact disk (CD) drive or digital versatile disk (DVD) drive, a flash memory, etc.), a communication interface (e.g., Bluetooth interface, infrared interface, network interface, optical interface, etc.), and numerous other elements and functionalities.

A computer processor of a computing system (142) may be an integrated circuit for processing instructions. For example, the computer processor may be one or more cores or micro-cores of a processor. The computing system (142) may also include one or more input devices, such as a touchscreen, keyboard, mouse, microphone, touchpad, electronic pen, or any other type of input device.

A communication interface of a computing system (142) may include an integrated circuit for connecting the computing system (142) to a network (not shown) (e.g., a local area network (LAN), a wide area network (WAN) such as the Internet, mobile network, or any other type of network) and/or to another device, such as another computing system (142).

Further, the computing system (142) may include one or more output devices, such as a display device (e.g., a liquid crystal display (LCD), a plasma display, touchscreen, organic LED display (OLED), projector, or other display device), a printer, a speaker, external storage, or any other output device. One or more of the output devices may be the same or different from the input device(s). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the invention.

A computing system (142) may be connected to or be a part of a network. The network may include multiple nodes. Each node may correspond to a computing system (142), or a group of nodes. By way of an example, embodiments of the disclosure may be implemented on a node of a distributed system that is connected to other nodes. By way of another example, embodiments of the invention may be implemented on a distributed computing system having multiple nodes, where each portion of the disclosure may be located on a different node within the distributed computing system. Further, one or more elements of the aforementioned computing system (142) may be located at a remote location and connected to the other elements over a network.

The robotic manipulating system (130) may use a tool (160) comprising an imaging device, (e.g., a monoscopic or stereoscopic endoscope, an ultrasonic probe in a medical example) to capture images of the worksite and output the captured images to an auxiliary system (140). Similar to other tools (160), a tool with an imaging device has a mechanical interface (not shown) allowing the imaging device to be coupled to the manipulator arm (150). The mechanical interface of different tools (160), such as the tool with the imaging device, may be the same or differ from each other. Accordingly, a mechanical adapter may be used where applicable to couple a tool (160) to the manipulator arm (150). Alternatively, a particular tool (160), such as a specialized imaging tool, may be mounted on a manipulator arm (150) specifically designed to accommodate such tools (160). The auxiliary system (140) may process the captured images in a variety of ways prior to any subsequent display. For example, the auxiliary system (140) may overlay the captured images with a virtual control interface prior to displaying the combined images to the user via the user control system (120). The robotic manipulating system (130) may output the captured images for processing outside the auxiliary system (140). One or more separate displays (144) may also be coupled with a computing system (142) and/or the auxiliary system (140) for local and/or remote display of images, such as images of the procedure site, or other related images.

Figures 2, 3:
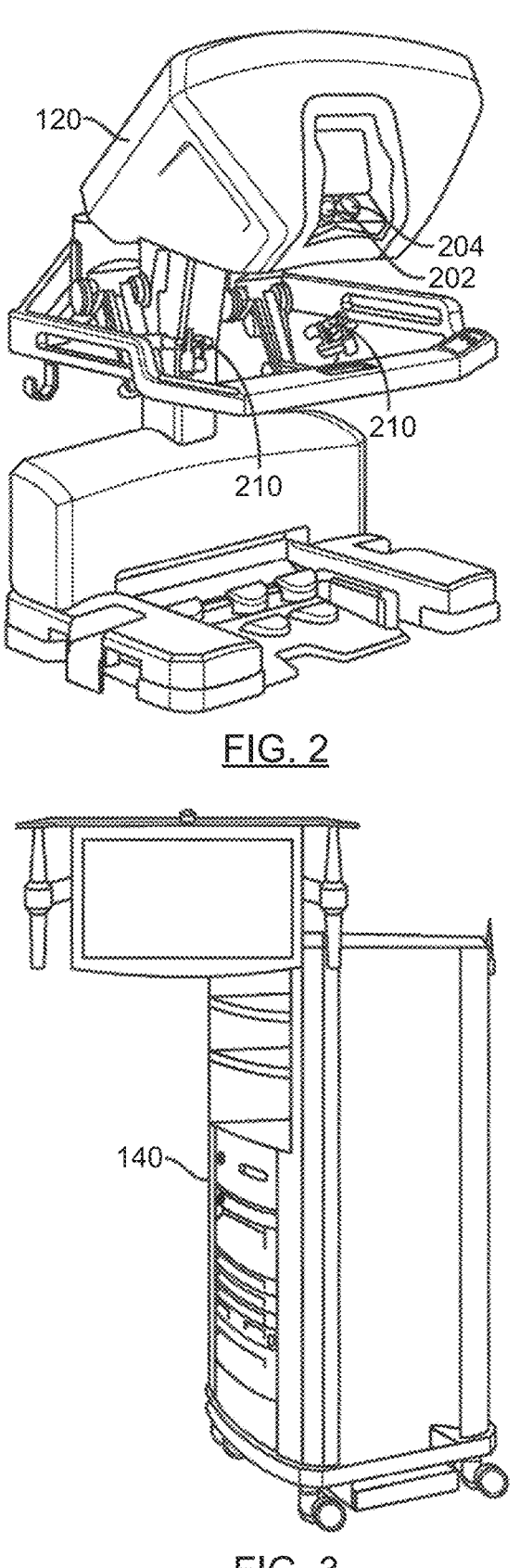
FIG. 2 shows a perspective view illustrating a user control system usable for inputting commands for the robotic procedure scenario of FIG. 1A, in accordance with one or more embodiments.
FIG. 3 shows a perspective view of an auxiliary system usable in the robotic procedure scenario of FIG. 1A, in accordance with one or more embodiments.

FIG. 2 shows a perspective view of an example user control system (120) usable as part of the computer-assisted system (100). The user control system (120) includes a left eye display (202) and a right eye display (204) for presenting the user (192) (shown in FIG. 1A) with a coordinated stereo view of the worksite that enables depth perception. The user control system (120) further includes two input control devices (210), which in turn causes the robotic manipulating system (130) (shown in FIG. 1A) to manipulate one or more tools. Although FIG. 2 shows the user control system (120) in the form of a console, an integrated display, and input control devices (210) mechanically grounded to the console, other implementations of the user control system (120) may comprise systems in other formats. For example, user control systems may comprise physically separate display(s), one, two, three, or more input control devices (210), and/or input control devices (210) not mechanically grounded to the rest of the user control system.

FIG. 3 shows a perspective view of the auxiliary system (140). The auxiliary system (140) may be communicatively coupled with one or more imaging devices comprising one or more tools (160) and may include a processor (not shown) to process captured or received images for display, such as to a display of a user control system (120) or to another suitable display located locally and/or remotely. For example, where a stereoscopic or depth-capable imaging device is used, the auxiliary system (140) may process the captured images so as to present coordinated stereo images or depth-enhanced images of the worksite.

Figure 4A:
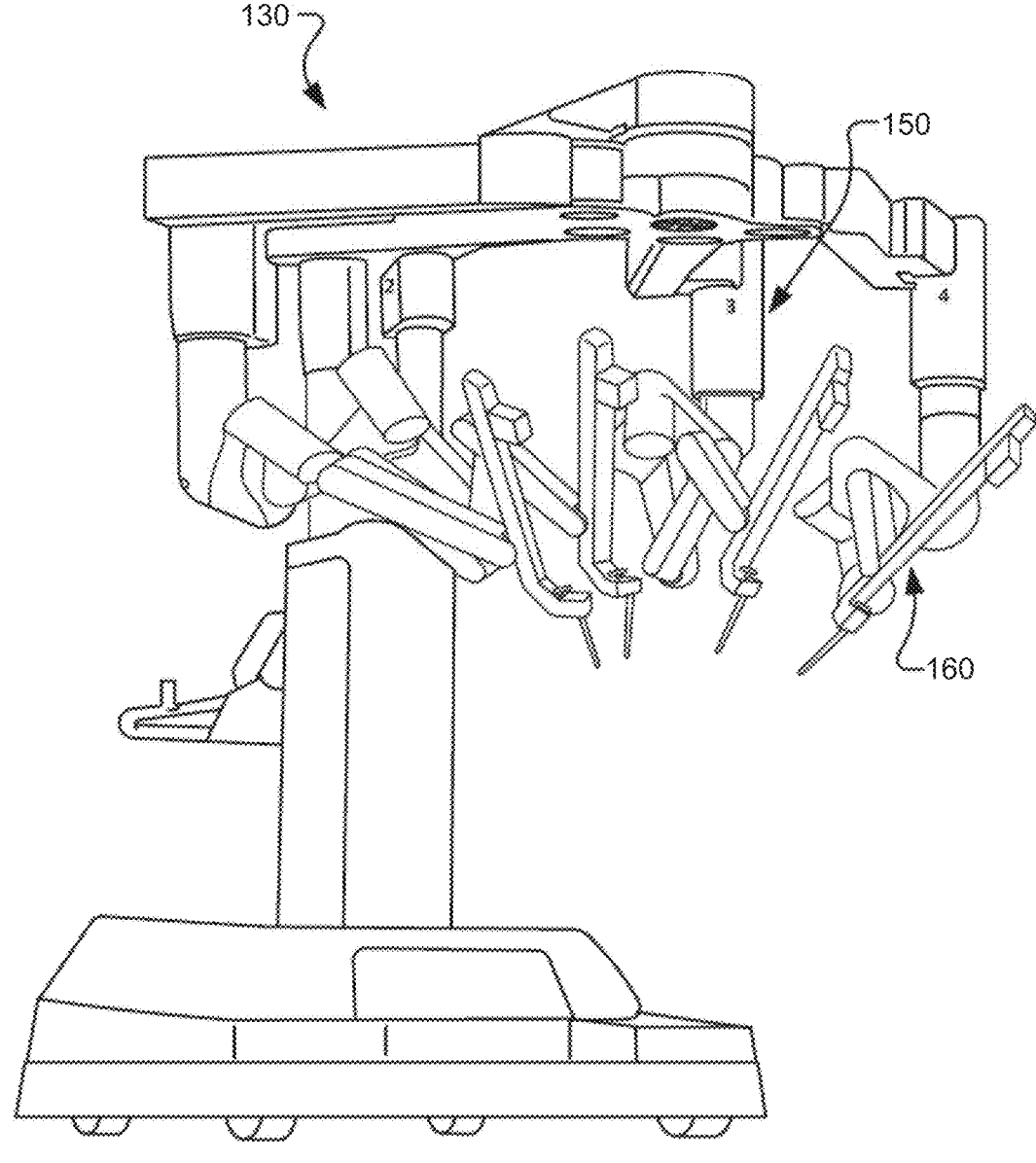
FIG. 4A shows a perspective view of a robotic manipulating system, in accordance with one or more embodiments.

FIG. 4A shows a robotic manipulating system (130) having a plurality of manipulator arms (150), each manipulator arm (150) configured to support a tool (160) at a distal portion of the manipulator arm (150). The robotic manipulating system (130) as shown includes four manipulator arms (150), each of which may be used to support one or more tools. A more detailed description of a manipulator arm (150) is provided below with reference to FIG. 5, and a more detailed description of a tool (160) is provided below with reference to FIG. 6. In minimally invasive medical example, the tools (160) may be positioned and manipulated through an aperture such as natural orifices or incisions in the patient so that a kinematic remote center is maintained at the incision; this can help reduce the required size of the aperture, collisions or forces applied to tissue surrounding an aperture, etc. Images of the worksite may include images of the distal ends of the tools (160) when the tools (160) are positioned within the field-of-view of an imaging device comprising a tool (160).

A variety of tools (160) of different types and differing end effectors (for tools comprising end effectors) may be used. One or more of the tools (160) may be removed and/or replaced during a procedure.

In minimally invasive surgical scenarios, an elongated shaft of a tool (160) allows the end effectors and the distal end of the shaft to be inserted distally into a surgical worksite through a minimally invasive aperture, such as a natural orifice or an incision. The surgical worksite may be insufflated. Movement of the end effectors within the patient is often effected, at least in part, by pivoting of the tool (160) about the location at which the shaft passes through the minimally invasive aperture. Accordingly, manipulator arms (150) may move the proximal portion of the tool (160) outside the patient so that the shaft extends through the minimally invasive aperture to provide a desired movement of end effector. Hence, manipulator arms (150) may undergo movement outside the patient.

Figure 4B:
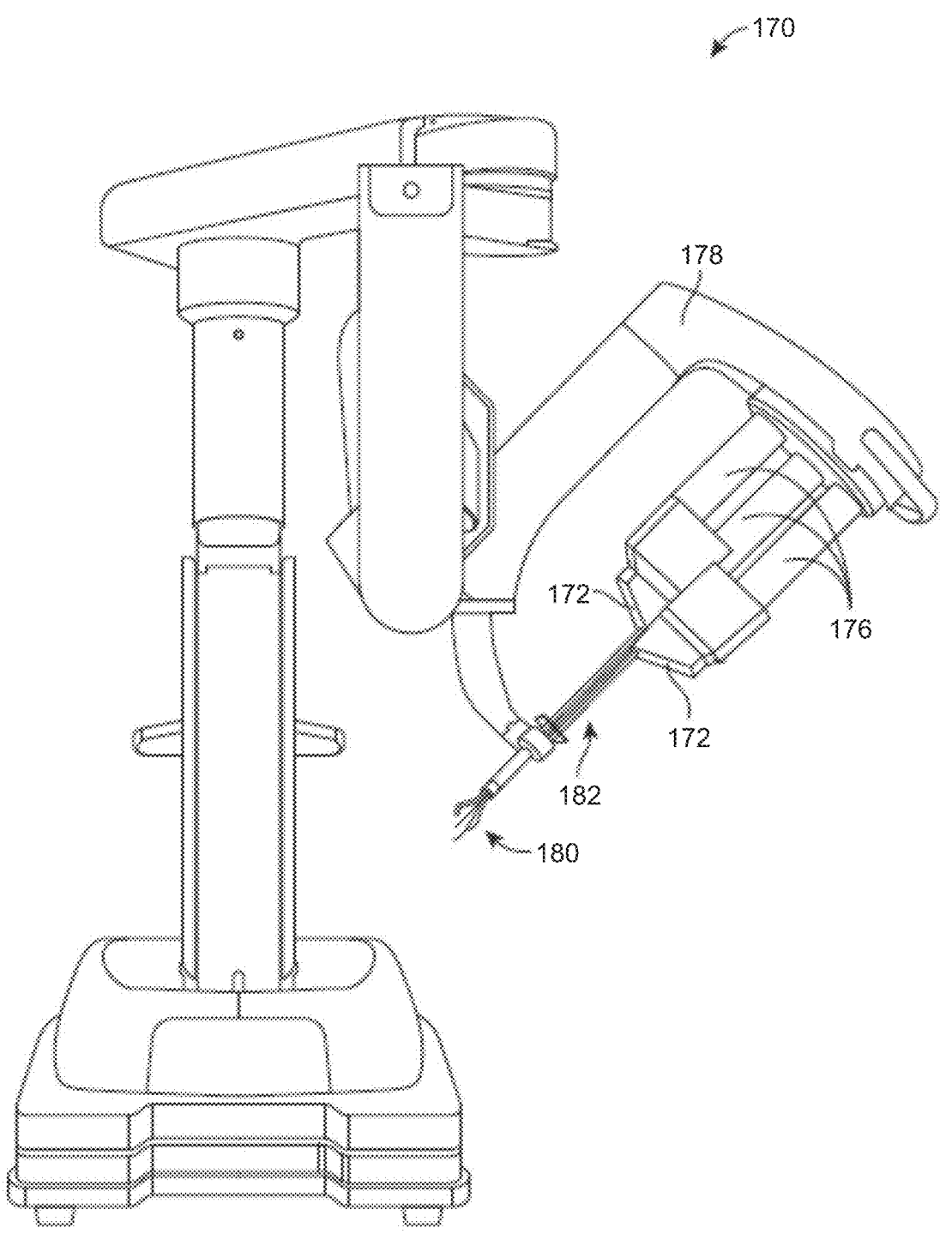
FIG. 4B shows a perspective view of a robotic manipulating system, in accordance with one or more embodiments.

FIG. 4B shows a robotic manipulating system (170) configured to support tools (172), in accordance with one or more embodiments. Each of the tools (172) is mounted to a manipulator arm (176) disposed on a support arm (178). In a medical scenario, a sterile barrier (not shown in FIG. 4B) including a drape and instrument adaptors may be disposed between a patient (not shown) and the support arm (178). The support arm (178) and the manipulator arms (176) may thus be disposed outside a sterile environment for the patient, while the tools (172) are disposed inside the sterile environment.

Like the tools (160) discussed in conjunction with FIG. 4A, the tools (172) may vary in structure and purpose but may be removable, replaceable, and/or interchangeable. Each tool (172) generally includes an end effector (180) and a shaft (182). The end effectors (180) may have different designs to implement different functions, including those described in conjunction with FIG. 6. The manipulator arms (176) may include actuators such as drive motors that provide mechanical power to actuate mechanical structures in the tools (172).

Figure 5:
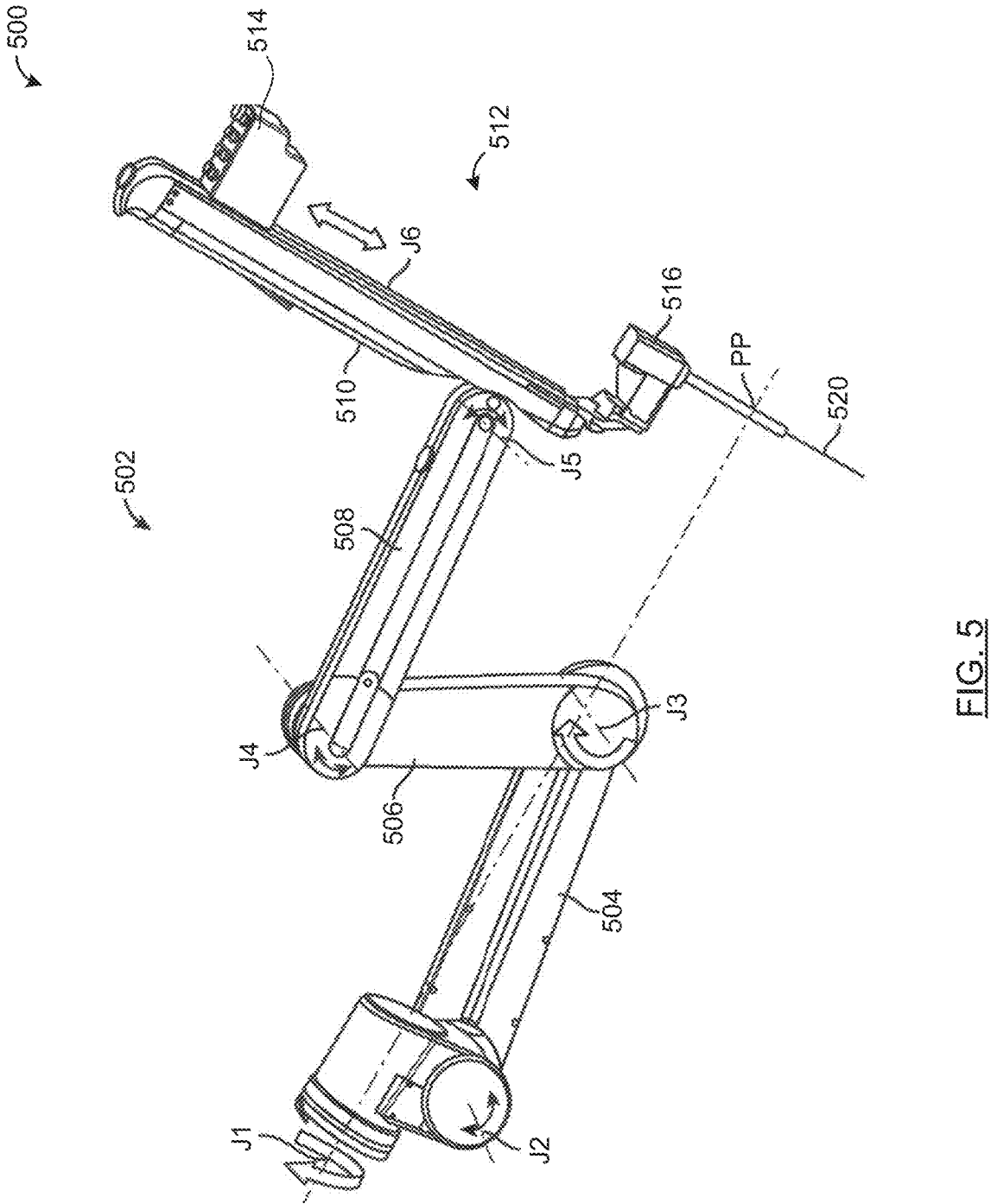
FIG. 5 shows an example of a manipulator assembly, in accordance with one or more embodiments.

An example of a manipulator assembly (500) in accordance with embodiments of the present disclosure is shown in FIG. 5. A manipulator assembly (500) includes a manipulator arm (502) and may further include a tool mounted to the manipulator arm (502) (in FIG. 5, only an axis of the tool (e.g., 520), but not the tool itself, is shown). Thus, the term "manipulator assembly (500)" may be used to indicate the manipulator arm (502) with the tool in some instances, and the manipulator arm (502) without the tool in other instances. Other components may be included in the manipulator assembly (500). As described above, during operation, the manipulator arm (502) generally supports a tool (520) and effects movements of the tool (520). In the example shown in FIG. 5, the manipulator arm (502) comprises a tool holder (514) to facilitate removal and replacement of one or more tools (520).

As may be understood with reference to FIG. 4A and FIG. 4B, in some embodiments, manipulator arms (e.g., (502), other manipulator arm designs) are proximally mounted to a base of the manipulating system (e.g., (130), (170)). Alternatively, manipulator arms (502) may be mounted to separate bases that may be independently movable; for example, one or more manipulator arms (502) may be mounted to single-manipulator arm carts, be provided with mounting structures for mounting directly or indirectly to an operating table or at one or more locations (e.g. by being clamped to a rail or other component, by being mounted to the wall or floor, etc.) Typically, a manipulator arm (502) includes a plurality of links and associated joints extending between the proximal base and the distal portion of the manipulator arm (502).

In embodiments such as shown for example in FIG. 5, the manipulator arm (502) includes one or multiple joints (such as revolute joints J1, J2, J3, J4, and J5, and prismatic joint J6) coupling one or multiple links (504, 506, 508, and 510). A link (510) of the manipulator arm (502) may be configured to couple with a cannula (516) through which the shaft of the tool (520) extends, and the link (510) may include a tool holder (514) to which the tool attaches. In the example shown in FIG. 5, actuation of the degrees of freedom of the tool (520) is provided by actuators of the manipulator arm (502). These actuators may be integrated in the tool holder (514), or their motive forces or torques may be transmitted through the tool holder (514) to the tool (520).

The joints of the manipulator arm, in combination, may or may not provide the manipulator arm with redundant degrees of freedom. A manipulator arm with one or more redundant degrees of freedom has a plurality of joints such that the plurality of joints may be driven into a range of differing configurations for a given position and/or orientation of a portion of the manipulator arm, or of an abstract feature referenced to a portion of the manipulator arm (e.g. a remote center of motion (PP) at a location defined relative to a distal portion of the manipulator arm). For example, a manipulator arm may be maneuvered into differing configurations while an end effector of a tool coupled to the tool holder, a remote center of motion, and/or another feature, maintains a particular state. Example states maintained include a given position, orientation, and/or velocity of the end effector.

Figure 6:
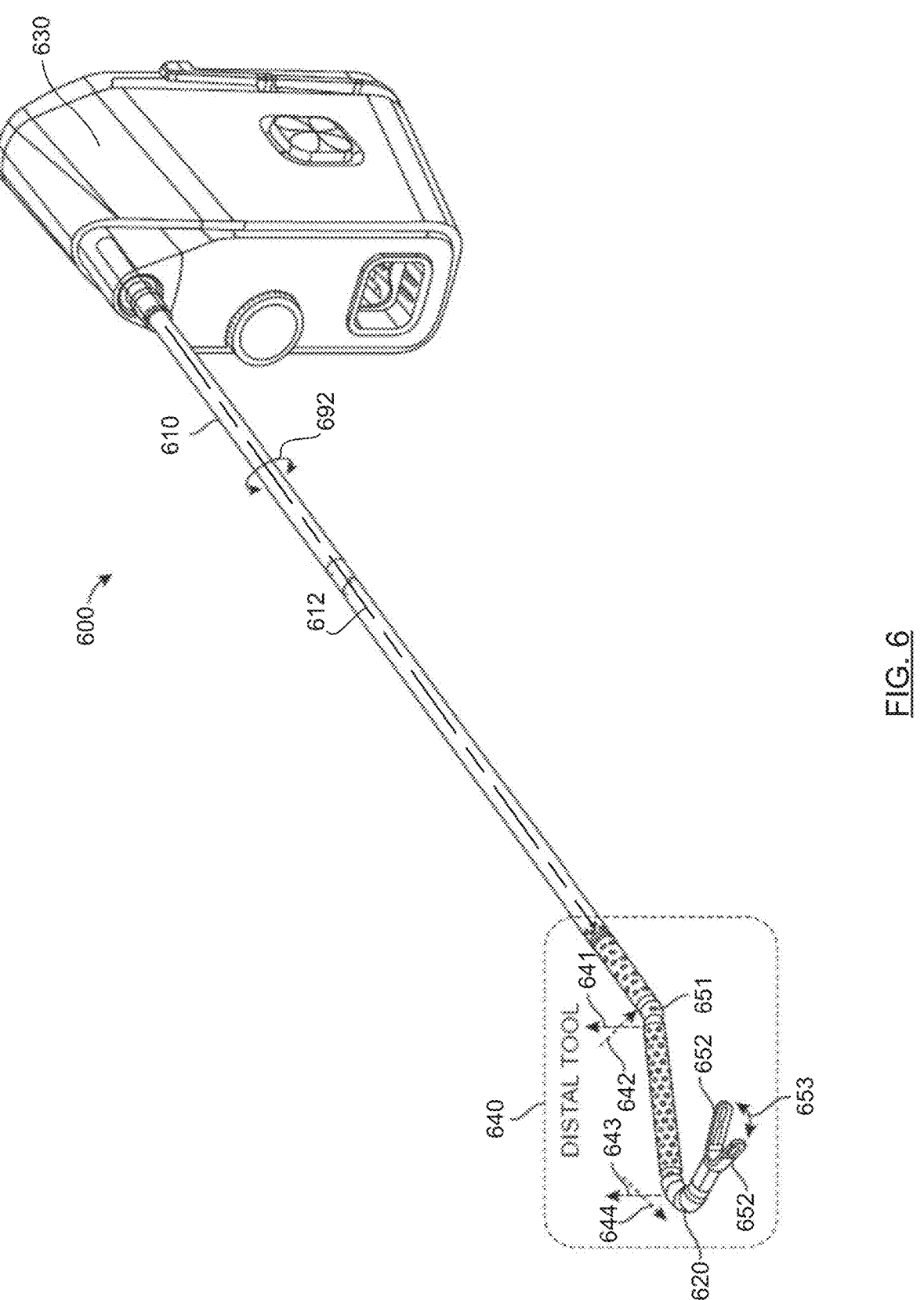
FIG. 6 shows a perspective view of a tool, in accordance with one or more embodiments.

FIG. 6 shows an example of a tool (600) (also called instrument (600)), in accordance with one or more embodiments. The tool (600) includes a shaft (610), and an end effector (640) located near a first end of the shaft (610). A housing (630), arranged releasably to couple the tool (600) to a manipulator arm (e.g., manipulator arm (150, 176, 502)), is located at an opposed end of the shaft (610). In the illustrated implementation, the end effector (640) has six degrees of freedom of movement relative to the housing (630). Specifically, the six degrees of freedom may correspond to: pitch and yaw rotations of a portion of the end effector (640) about two respective perpendicular axes (641) and (642) associated with a first joint or wrist mechanism (651); pitch and yaw rotations or movement of jaws (652) relative to two respective perpendicular axes (643) and (644) associated with a second joint or wrist mechanism (620); opening or closing movement (653) of jaws (652) for "grip" actuation; and "roll" rotations (692) of instrument shaft (610) about its insertion axis (612). In the example shown, the insertion axis is parallel with a central axis of the instrument shaft (610). Other tools may have more, fewer, or different degrees of freedom of movement than the tool shown in FIG. 6, without departing from the disclosure. The tool (600) is designed to be releasably mounted to a manipulator arm. The manipulator arm includes a prismatic joint (J6) that may be driven to translate the tool mounted to the tool holder along an axis that may be an in/out axis, or insertion axis (612). The housing (630) may include physical input elements that are rotatable or translatable to drive joints of the tool (600). An example of such is described in U.S. Pat. No. 6,394,998, entitled "Surgical Tools for Use in Minimally Invasive Telesurgical Applications". The manipulator arm (e.g., 150, 176, 502) may include drive elements such as disks or sliders or protrusions for coupling with the physical input elements to drive the tool (600). The drive elements may be driven by actuators, e.g., electrical motors, which respond to inputs from the associated input control devices (e.g. input control devices (210) in FIG. 2) to drive the tool (600) as dictated by movement of the input control devices (210) or any other control signal, such as to move the end effector (640) to a desired orientation and/or position. Furthermore, appropriately positioned sensors, e.g., encoders, potentiometers, etc., may be provided to enable measurement of the joint positions of the tool (600) or the manipulator arm (e.g., (150), (176), (502)). The actuators and sensors may be disposed in the tool (600), the tool holder (e.g., 514), the manipulator arm (e.g., (150), (176), (502)), or elsewhere.

Different tools (600) may be equipped with no end effectors, or with different end effectors (640) with different geometries (e.g., different shapes or sizes), different degrees of freedom, and/or different functions. An end effector may have a single finger or two or more fingers. Examples for end effectors with a single finger include, but are not limited to, scalpels, cautery electrodes, irrigation or suction devices, endoscopes (which may or may not have a wrist), etc. Examples for end effectors with two fingers include, but are not limited to forceps, clip appliers, scissors, dissection tools, pliers, graspers, jawed cautery tools, needle drivers, etc. or the like. Fingers of the end effector (640) may be individually angularly displaceable, thereby not only allowing an opening and closing of the end effector, but also enabling an angular displacement to change the orientation of the end effector (640) as a whole, relative to another part of the tool (e.g. the wrist mechanism (620, 651), the shaft (610), etc.).

While FIG. 1A, FIG. 1B, FIG. 2, FIG. 3, FIG. 4A, FIG. 4B, FIG. 5, and FIG. 6 show various physical configurations of components of example computer assisted systems, other configurations may be used without departing from the scope of the invention. For example, while a particular configuration of a robotic manipulation system with manipulator arms is shown, embodiments of the disclosure generalize to and are applicable to any type of robotic manipulation system, e.g., with a single manipulator arm holding a single tool, with a single manipulator arm holding multiple tools, etc. As another example, the functionality performed by a single component may be performed by two or more components. Further, while the components are described in context of surgical scenarios, embodiments of the disclosure may be equally applicable to other domains that involve robotic manipulation.

Figures 7A, 7B:
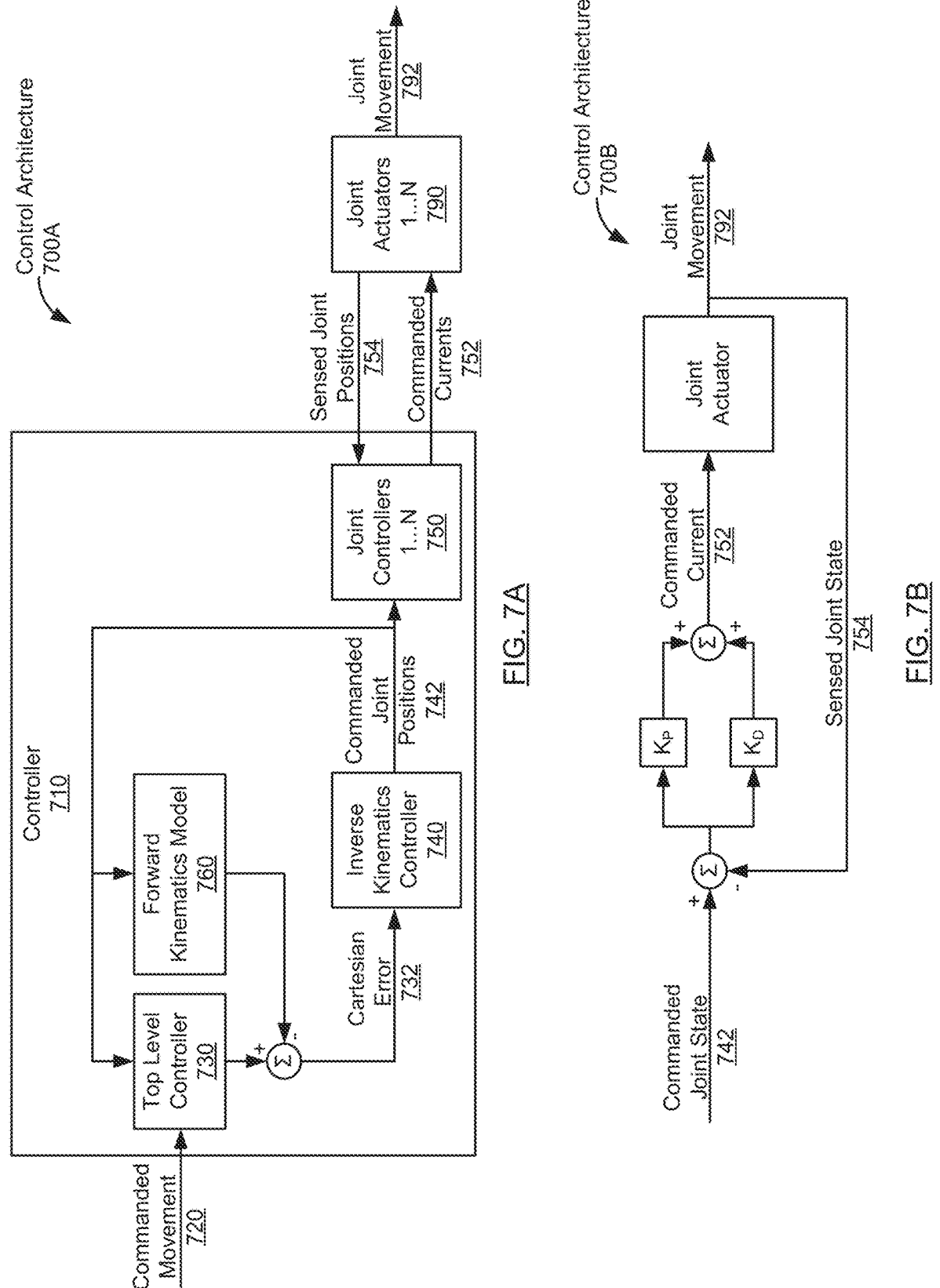
FIG. 7A and FIG. 7B show control architectures for controlling a computer-assisted system, in accordance with one or more embodiments.

FIG. 7A, shows an example control architecture for controlling a manipulator assembly including a manipulator arm, which may have a tool mounted thereon, in accordance with one or more embodiments. Those skilled in the art will appreciate that other control architectures may be used without departing from the disclosure. Further, in the illustrated control architecture, particular signals (e.g. positions) are exchanged between blocks of the control architecture. Other signals (e.g., velocities, accelerations, forces, etc.) may be used, without departing from the disclosure. Also, the control architecture may implement one, two, three, or more different modes (not shown). For example, during a "following" mode, a task is performed by a manipulator assembly under the teleoperated control of input control devices (210) operated by a user as shown in FIG. 2. The joint(s) of the robotic manipulator assembly may be position-controlled, velocity-controlled, etc., and may or may not be back-driven depending on the physical design of the manipulator assembly and the control scheme. As another example, in a "tool exchange" mode, one or more joints of a manipulator assembly may be "floating", allowing an assistant to readily externally articulate these one or more joints, such as by backdriving these one or more joints. A floating joint may be backdriven by an externally applied force without a control algorithm counteracting the backdriving or a braking force counteracting such backdriving. As another example, in a "clutch" mode, one or more active joints of a manipulator assembly may be floating joint by being controlled to be compliant to external manipulation. As a specific example, in a "clutch mode", a commanded position for a floating joint can be regularly updated to the current position, to assist external manipulation.

Various types of "following", "tool exchange", "clutch", or other modes may be implemented. For example, in one embodiment of the disclosure, in a clutch mode the system floats one or more joints manipulator arm such that externally applied forces to the manipulator arm readily moves a remote center of the manipulator arm relative to a world frame of reference, and the manipulator arm is not controlled to concurrently maintain a position of the end effector relative to the world frame of reference. As another example, in another embodiment of the disclosure, in a clutch mode the system controls one or more joints of a manipulator arm such that externally applied forces to the manipulator arm readily moves a remote center of the manipulator arm relative to a world frame of reference, while preventing movement of the tool or end effector relative to the world frame of reference. A system may implement any combination of back-drivable or non-backdrivable modes, including one or more of the modes described above and additional modes, without departing from the disclosure A user may apply a force to a link distal to the floating joint, causing the backdriving of the floating joint. A floating joint may be controlled to provide gravity-compensation, friction compensation, and/or to impose other characteristics such as a certain level of damping.

A combination control mode may also be implemented during operation of a manipulator assembly. For example, in a control mode, some joints may be position controlled to resist or rebound from external articulation of those joints, while other joints may be floating and facilitate external articulation of those other joints. Also, one or more joints of the manipulator assembly may be passive, i.e., not position or velocity controlled at all (but may be with brakes partially or completely applied). Passive joints may be manually operated. Joints may also include joint sensors, such that the full kinematics of the manipulator assembly may be obtained. In some embodiments, passive joints may contain actuators for supplying gravity compensation, friction compensation, or other utility not including actively driving the motion of the passive joint.

In one or more embodiments, the joint movements of the manipulator assembly are controlled by driving one or more joints by a controller commanding actuators (e.g., motors, solenoids, etc.) of the manipulator assembly, the joint movements being calculated by a processor of the controller. Mathematically, the controller may perform at least some of the calculations of the joint commands using vectors and/or matrices, some of which may have elements corresponding to positions, velocities, and/or forces/torques, etc. of the joints. The range of alternative joint configurations available to the processor may be conceptualized as a joint space. The joint space may, for example, have as many dimensions as the manipulator assembly has degrees of freedom, and a particular configuration of the manipulator assembly may represent a particular point in the joint space, with each coordinate corresponding to a joint state of an associated joint of the manipulator assembly.

As used herein, the term "state" of a joint or multiple joints refers to the control variables associated with the joint or the multiple joints, respectively. For example, the state of an angular joint may refer to the angle defined by that joint within its range of motion, to the angular velocity of the joint, and/or to the angular acceleration of the joint. Similarly, the state of an axial or prismatic joint may refer to the joint's axial position, to its axial velocity, and/or its axial acceleration. While one or more of the controllers described herein include position controllers, they often also have velocity control aspects. Alternative embodiments may rely primarily or entirely on velocity controllers, force controllers, acceleration controllers, etc. without departing from the disclosure. Many aspects of control systems that may be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, etc.

The control architecture (700A) of FIG. 7A includes a controller (710) that drives actuator mechanisms (790) of the manipulator assembly based on a commanded movement (720). Any number of actuator mechanisms (790) may be driven. An actuator, combined with other elements such as sensors, or gears, pulleys and cables or wires, and/or other transmission elements, etc., may form an actuator mechanism of a joint, and the joint state can be changed by being actuated by the actuator mechanism.

The commanded movement (720) may be a commanded position and/or velocity of one or more features in the work-space, which may be modeled in Cartesian-coordinate space (referred to herein as Cartesian-space). The commanded movement (720) may be, for example, a movement command (e.g., in the form of a position and/or velocity) received from the user control system (120), or any other movement command, for one or more features of, or referenced to, the manipulator arm or a tool coupled to the manipulator arm. A feature may be any feature physically on the manipulator assembly or may be an abstraction physically off the manipulator assembly (e.g. a point or plane referenced to the manipulator assembly), which may be used to define a control frame to be articulated using control inputs. Examples of features on the manipulator assembly include features of a tool (e.g., an end effector tip, a central point on the end effector, or a clevis of the end effector), a feature of the manipulator arm (e.g., a tool holder configured to physically couple with a removable tool), etc. Another example of a feature of the manipulator assembly is a reference point in empty space which is exactly a certain distance and angle away from a tip of the tool.

The controller (710) may include a top level controller (730), an inverse kinematics controller (740), joint controllers (750), and a forward kinematics model (760). Each of these components is subsequently described.

The top level controller (730), in accordance with one or more embodiments, includes instructions in the form of computer readable program code to receive the commanded movement (720), and to convert the commanded movement (720) into positions in a Cartesian reference frame. The steps performed to convert the commanded movement (720) into Cartesian positions depend on the format in which the commanded movement (720) is provided.

The inverse kinematics controller (740), in accordance with one or more embodiments, to convert commanded Cartesian positions into commanded joint positions (742) (e.g., translational positions for prismatic joints, joint angles for rotary joints, etc.). The operations by the inverse kinematics controller may be performed in the velocity domain and compute commanded joint velocities. The inverse kinematics controller (740) may integrate the computed joint velocities to obtain command joint positions (742).

The Cartesian error (732) may be a combination of the Cartesian positions provided by the top level controller (730), as previously discussed, and Cartesian positions provided by a forward kinematics model (760), discussed below. More specifically, the Cartesian positions provided by the forward kinematics model (760) may represent an estimate of an actual or current position (e.g., of an end effector), in Cartesian space, of the manipulator assembly. This estimate may be subtracted from the Cartesian positions representing the commanded movement, to obtain the difference to be compensated for, to be used as the control input to the inverse kinematics controller (740).

While generally there may not be a closed form relationship which maps a desired Cartesian space position to an equivalent joint-space position, a closed form relationship between the Cartesian space velocity and joint-space velocities typically exists. The kinematic Jacobian is the matrix of partial derivatives of Cartesian space position elements with respect to joint space position elements. The kinematic Jacobian (J) may be used to map joint-space velocities (dq/dt) to Cartesian space velocities (dx/dt), e.g., end effector velocities.

Thus, even when there is no closed-form mapping between input and output positions, mappings of the velocities may iteratively be used by the inverse kinematics controller (740) to implement a movement of the manipulator assembly based on a commanded trajectory.

Each of the joint controllers (750), in accordance with one or more embodiments, convert a received commanded joint position (742), such as a linear or angular joint position, into an actuator command (752) to drive one of the actuator mechanisms (790) and produce a joint movement (792). The actuator command (752) may be in any form appropriate for the actuator mechanism (790). For example, the actuator command (752) may comprise a voltage, a digital value, or other signal communicated to a motor controller of a motor-type actuator mechanism. One joint controller (750) may be used to control each actuator mechanism (790). The joint movements (792) of all actuator mechanisms through the kinematics of the manipulator assembly may produce a manipulator arm movement that reflects the commanded movement (720). An example of a joint controller (750) is provided in FIG. 7B.

The forward kinematics model (760), in accordance with one or more embodiments, convert the sensed joint states (754) into other forms, such as joint positions or velocities into Cartesian positions or velocities, as previously discussed.

Any part of the controller (710), or the entirety of the controller (710), may be implemented in hardware, software, or a combination of hardware and software. For example, part or all of the controller (710) may be implemented in the form of computer readable program code configured to perform the operations described for the controller (710). The controller (710) may be implemented on one or more computing systems. These one or more computing systems may be based on digital signal processors (DSPs), central processing units (CPUs), etc. An example computing system is described with reference to FIG. 1B.

Figure 8:
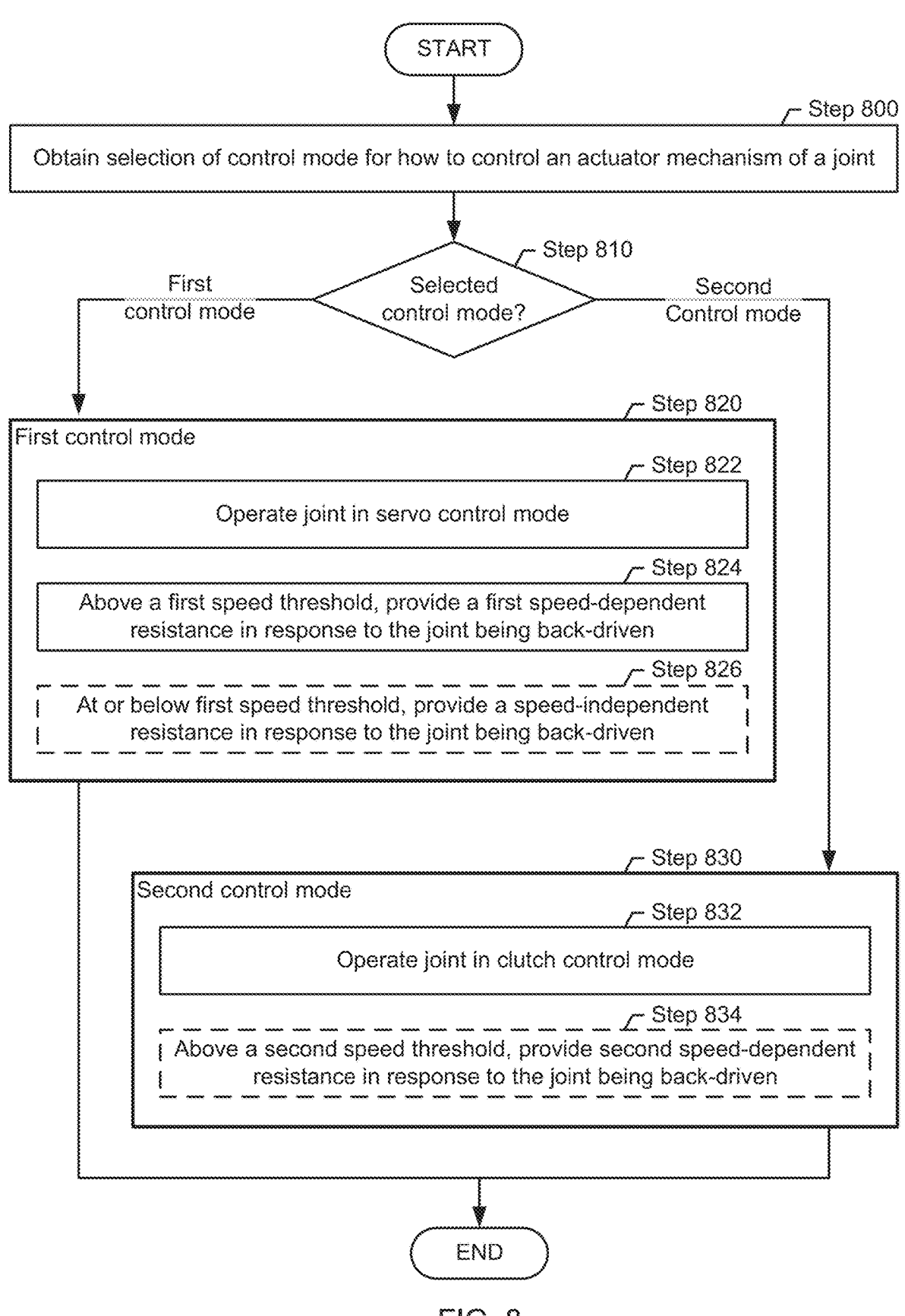
FIG. 8 shows a flowchart describing a method for providing a controlled resistance in backdrivable joints, in accordance with one or more embodiments.

In one or more embodiments, the controller (710) is further configured to perform at least one of the steps described in FIG. 8.

Turning to FIG. 7B, a control architecture (700B) of a joint controller, in accordance with one or more embodiments, is shown. In the example, a closed-loop PD (proportional-derivative) control structure is used to control a joint position based on a commanded joint position input.

The joint controller may receive a feedback signal in the form of a sensed joint state (754) (specifically, in this example, a sensed joint position), in case of the control architecture (700B)) from the associated actuator mechanism (790) to enable closed-loop control. The joint state (754) may be derived from signals obtained from a sensor attached to the joint. Such a sensor may be, for example, an incremental encoder, a shape sensor, or a hall sensor of the joint or actuator mechanism. A state observer or estimator (not shown) may be used. The PD control structure uses two control gains ($K_P$, $K_D$), operating on a difference between the commanded joint position (742) and the sensed joint position (i.e. an error signal) and their derivatives, respectively, to produce an actuator command (752). In one or more embodiments of the disclosure, the actuator command (752) is limited, and accordingly the resulting joint torque or force is limited as well. The limit may be based on hardware limitations such as a maximum acceptable motor current. The limit may further be software configurable.

Accordingly, the motor current (and the resulting motor torque or force) may increase linearly with the position error between the commanded joint position (742) and the sensed joint position (754) as dictated by the proportional control gain ($K_P$) only until the saturation limit is reached. Beyond the limit, the motor current is constant. A higher $K_P$ may result in a relatively small position error being sufficient for reaching the saturation limit, whereas a lower $K_P$ may result in a relatively larger position error being required for reaching the saturation limit. In one embodiment of the disclosure, a relatively high $K_P$ is used to obtain a responsive position control of the joint with a limited steady state error. Accordingly, an increase in the position error may quickly result in reaching the saturation limit. While the control architecture (700B) uses a proportional derivative (PD) controller, other controllers such as proportional integral derivative (PID), full state feedback, sliding mode, or various other control schemes, may be used, without departing from the disclosure. Further, while the control of a joint position is illustrated, other variables such as velocity, torque or force may be controlled, without departing from the disclosure.

The previously described backdriving of a joint may occur in multiple different control modes for how to control the actuator mechanism associated with the joint. An implementation may be configured with one, two, three, four, or more control modes that allow backdriving of a joint. For illustration, the below text describes three different example control modes that allow backdriving of a joint. These control modes are described as based on the control architecture (700B) in FIG. 7B, and other control architectures are also possible. A system may be configured with any one of these three control modes, any two of these three control modes, all three control modes, or some other combination of control modes matching or different from the three control modes described below.

As an example, a system can be implemented with a backdrivable control mode comprising a slip-lock control mode. The slip-lock control mode is more fully described in U.S. Provisional Patent Application No. 62/826,780 and in PCT Patent Application No. PCT/US2020/025481, the full disclosures of which are incorporated herein by reference. Assume, for example, that PD controllers, as introduced in FIG. 7B, are used for the control of the actuator mechanism of a manipulator arm or a manipulator assembly including the manipulator arm and a tool. One PD controller may be used to control one actuator mechanism of a manipulator arm segment. The controlling may, for example, involve holding the joint at a commanded joint position (e.g., the commanded position may be provided as the commanded joint state (742), in FIG. 7B). As discussed with reference to FIG. 7B, the proportional control gain of the PD controller may operate on a deviation of the actual joint position (e.g., the sensed or estimated joint position) from the commanded position. In response to the deviation, an actuator command for driving the actuator mechanism may be generated or modified, and the actuator mechanism, commanded by the actuator command, may produce an appropriate amount of torque or force (e.g., a motor torque or force supplied at the output of the actuator or joint torque or force)). For example, an actuator command may comprise or cause a commanded current for a motor-type actuator, and cause a torque output that is proportional to the commanded current. Accordingly, a larger difference between the commanded joint position and the sensed joint position results in a stronger torque produced by the actuator mechanism. Thus, a PD controller-based control loop may emulate characteristics of a linear spring in part: The farther apart the commanded and the actual joint positions are, the more energy is stored in the spring, due to the PD controller's increased effort to compensate for the difference. The coefficient of the spring may be governed by the proportional control gain ($K_P$). In one or more embodiments, a defined threshold is used to distinguish two behaviors of the joint: (1) When the deviation does not exceed the defined threshold, the PD controller compensates for the deviation by driving the actuator mechanism in a direction countering the deviation. In other words, the actuator is controlled based on the commanded state. (2) When the deviation exceeds the defined threshold, the commanded state may be updated to be closer to the actual state, thereby reducing the deviation to an acceptable level, below the defined threshold. In other words, the commanded state may be adjusted to generate an adjusted commanded state, where the difference between the adjusted commanded state and the actual state is smaller than the deviation. The adjusted commanded state is then used to control the actuator. The adjusted commanded state may be chosen to, for instance, maintain a saturated output force/torque while minimizing deviation between adjusted command and actual states, with the defined threshold governing the saturated output force/torque.

The defined threshold may be set with respect to a commanded position or, more generally, a commanded state. In this configuration, when a force or torque associated with an external articulation (e.g., when a user applies a force to a link distal to the joint) results in a deviation of the sensed joint position from the commanded joint position exceeding the defined threshold, the joint may be backdriven. Alternatively, when a force or torque associated with an external articulation results in a deviation of the sensed joint position from the commanded joint position not exceeding the deviation threshold (e.g., as a result of a smaller force being applied), the joint may counter the force in a spring-like manner, without changing the commanded joint position. The amount of force needed to cause a change in the commanded position may depend on various factors. For example, for a higher defined threshold, more force would need to be applied than for a lower defined threshold. When the defined threshold is set to a very low value (close to zero), a backdriving may be possible with very little force or torque applied to the joint. Also, for a higher proportional control gain ($K_P$) more force would need to be applied than for a lower error threshold, because $K_P$ is responsible for the spring-like characteristics of the joint while below the error threshold, with a higher $K_P$ implementing a stiffer spring.

Accordingly, the characteristics of the backdriving behavior of the joint may be modulated through adjustment of the error threshold and/or $K_P$.

As an example, a system can be implemented with a backdrivable control mode comprising a position hold mode. Assume, for example, that PD controllers, as introduced in FIG. 7B, are used for the control of the actuator mechanism of a manipulator arm or a manipulator assembly including the manipulator arm and a tool. A PD controller may be used to control an actuator mechanism configured to move a first joint of the manipulator arm. The controller may, for example, control the actuator mechanism to hold the joint at a commanded joint position (e.g., the commanded position may be provided as the commanded joint state (742), in FIG. 7B). As discussed with reference to FIG. 7B, and as discussed for the slip-lock control mode, the proportional control gain of the PD controller may operate on a deviation of the actual joint position (e.g., the sensed or estimated joint position) from the commanded position. In response to the deviation, an actuator command for driving the actuator mechanism may be generated or modified; the actuator mechanism, commanded by the actuator command, may produce an appropriate amount of linear force or rotary torque (e.g., a torque supplied at the output of the actuator or a drivetrain driven by the actuator)). Accordingly, a larger difference between the commanded joint position and the sensed joint position results in a stronger force or torque produced by the actuator mechanism, as previously described for the slip-lock control mode. In one or more embodiments, once the deviation exceeds a defined threshold, the PD controller is also configured to prevent the force or torque from increasing further, such that a plateau is reached. This plateau, beyond the defined threshold, may be substantially position and speed-independent. In one or more embodiments, the PD controller is not configured to with such a defined threshold, or not configured to prevent the force or torque from increasing if the deviation exceeds the defined threshold.

As an example, a system can be implemented with a backdrivable control mode comprising a clutch control mode. For example, in an embodiment, PD controllers, such as introduced in FIG. 7B, are used for the control of the actuator mechanism of a manipulator assembly. One PD controller may be used to control one actuator mechanism of a manipulator arm segment. Referring to FIG. 7B, when an actuator mechanism is in a clutch control mode, the commanded joint position (742) may be set to match the sensed joint position (754). Because the proportional control gain of the PD controller operates on a deviation of the actual joint position (e.g., the sensed or estimated joint position) from the commanded joint position, the PD controller may produce a zero command (e.g. zero force, zero torque, zero current, etc.). The zero command may be modified to provide gravity and/or friction compensation, and as a result the joint associated with the actuator mechanism may float, as previously described.

The following paragraphs describe a method for providing a controlled resistance in backdrivable joints, based on the control modes, as discussed.

FIG. 8 shows a flowchart in accordance with one or more embodiments. The flowchart of FIG. 8 depicts a method for operating a robotic system, in accordance with one or more embodiments. More specifically, the method may be used to implement a controlled resistance in backdrivable joints. One or more of the steps in FIG. 8 may be performed by various components of the systems, previously described with reference to FIGS. 1A, 1B, 2, 3, 4A, 4B, 5, and 6. These figures describe particular manipulator arms and particular tools, the manipulator arms and tools having certain degrees of freedom. However, the subsequently described methods are not limited to a particular configuration of manipulator arms, tools and/or degrees of freedom. Instead, the methods are applicable to any type of manipulator arm, paired with any type of tool, used in any type of scenario. Further, one or more of the steps in FIG. 8 may build upon the control modes of the control architecture described in FIGS. 7A and 7B, A discussion of various applications and benefits follows the description of the method.

While the various steps in the flowchart are presented and described sequentially, one of ordinary skill will appreciate that some or all of the steps may be executed in different orders, may be combined or omitted, and some or all of the steps may be executed in parallel. Additional steps may further be performed. Furthermore, the steps may be performed actively or passively. For example, some steps may be performed using polling or be interrupt driven in accordance with one or more embodiments of the invention. By way of an example, determination steps may not require a processor to process an instruction unless an interrupt is received to signify that condition exists in accordance with one or more embodiments of the invention. As another example, determination steps may be performed by performing a test, such as checking a data value to test whether the value is consistent with the tested condition in accordance with one or more embodiments of the invention. Accordingly, the scope of the disclosure should not be considered limited to the specific arrangement of steps shown in FIG. 8.

Turning to the flowchart of FIG. 8, a series of steps that implement a method for providing a controlled resistance in backdrivable joints, is shown. The method may be repeatedly executed, e.g., in a loop. Although the flowchart of FIG. 8 shows steps performed for a single joint, the steps may be performed for multiple joints, without departing from the disclosure.

In Step 800, a selection of a control mode for how to control an actuator mechanism of a joint is obtained. Two control modes are shown for the method in the flowchart of FIG. 8: a first control mode and a second control mode. One or more additional control modes may exist, without departing from the disclosure. The selection of a control mode may be made by a user, e.g., by a user specifying the control mode. Alternatively, the control mode may be selected by a computing system, for example, by the top level controller of the control architecture of FIG. 7A. A control mode may be selected for an actuator mechanism of a single joint, or for actuator mechanisms of multiple joints. For example, as previously discussed, multiple joints may be "floated", when in a clutch control mode.

In Step 810, depending on which control mode is selected, the execution of the method proceeds with Step 820 to operate the joint in a first control mode, or with Step 830 to operate the joint in a second control mode. In one or more embodiments, the first control mode and the second control mode both allow an external articulation (e.g., as a result of a force being applied to a link distal to the joint) to reconfigure the manipulator arm, by backdriving the joint.

In Step 820, the controller commands the actuator mechanism to operate the joint in the first control mode. Operating the joint in the first control mode encompasses the execution of Steps 822 and 824, and optionally Step 826.

In Step 822, the joint is operated in a servo control mode. The servo control mode may be, for example, the slip-lock control mode or the position hold mode, as previously discussed in reference to FIG. 7B, or any other feedback controlled, backdrivable control mode.

In Step 824, above a first speed threshold, a first speed-dependent resistance (e.g., a motor force or torque or a joint force or torque) opposing the backdriving of the joint is provided. For a revolute joint, the first speed-dependent resistance may include a rotary force (e.g. a torque). For a prismatic joint, the first speed-dependent resistance may include a linear force (e.g. a force). In one embodiment, the first speed-dependent resistance simulates a speed-dependent damping response. The speed-dependent damping response may have any characteristic. For example, the first speed-dependent resistance may increase linearly or non-linearly (e.g., quadratically or exponentially) with the amount of speed of the backdriving exceeding the first speed threshold. Further, the slope of the speed-dependent damping response may be parameterizable to allow for a stronger or a weaker speed-dependence. Additional details regarding the speed-dependent damping response are provided below in reference to FIG. 9.

In Step 826, at or below the first speed-dependent threshold, a speed-independent resistance (e.g., a motor force or torque or a joint force or torque), opposing the backdriving of the joint, may be provided. Step 826 is an optional additional step for the FIG. 8 example. The speed-independent resistance may be provided in the slip-lock control mode, as previously described. The level of the speed independent resistance may be specified as a parameter. The parameter may be used to set the threshold up to which the PD controller-based control loop shows spring-like characteristics: The farther apart the commanded and the actual joint positions are allowed to be, based on the parameter, the more energy may be stored in the spring, thus resulting in a higher speed-independent resistance. If the acceptable difference between the commanded and the actual joint positions is set to zero, the speed-independent resistance may be zero or minimal (e.g., based on friction effects that exist regardless of the selected control mode).

In Step 830, the controller commands the actuator mechanism to operate the joint in the second control mode. Operating the joint in the second control mode encompasses the execution of Step 832, and optionally Step 834.

In Step 832, the joint is operated in a clutch control mode as previously discussed in reference to FIG. 7B.

In Step 834, above a second speed threshold, a second speed-dependent resistance opposing the backdriving of the joint is provided. The second speed threshold may be different from the first speed threshold, and/or the second speed-dependent resistance may be different from the first speed-dependent resistance. In one embodiment, the second speed-dependent threshold is higher than the first speed-dependent threshold. In one embodiment, the second speed-dependent resistance, like the first speed-dependent resistance, simulates a speed-dependent damping response and may have any characteristic as previously described. For a revolute joint, the second speed-dependent resistance may include a torque. For a prismatic joint, the second speed-dependent resistance may include a force. Step 834 is an optional additional step for the FIG. 8 example.

In one or more embodiments, the first speed threshold and/or the second speed threshold are below a back electromotive force (back EMF) speed limit. Accordingly, a user would experience the first and/or second speed-dependent resistance prior to reaching backdriven speeds that would result in back EMF effects provided by the actuator as previously discussed. The first and/or second speed-dependent resistance may provide haptic feedback to the user. In some embodiments, the user may use the first and/or second resistance as an indication that a further increase of the backdriven speed is undesirable, and the user may choose to avoid causing a further increase in the backdriven speed. Accordingly, the availability of the first and/or second speed-dependent resistance may help the user avoid reaching backdriven speeds beyond the back EMF speed limit.

Figure 9:
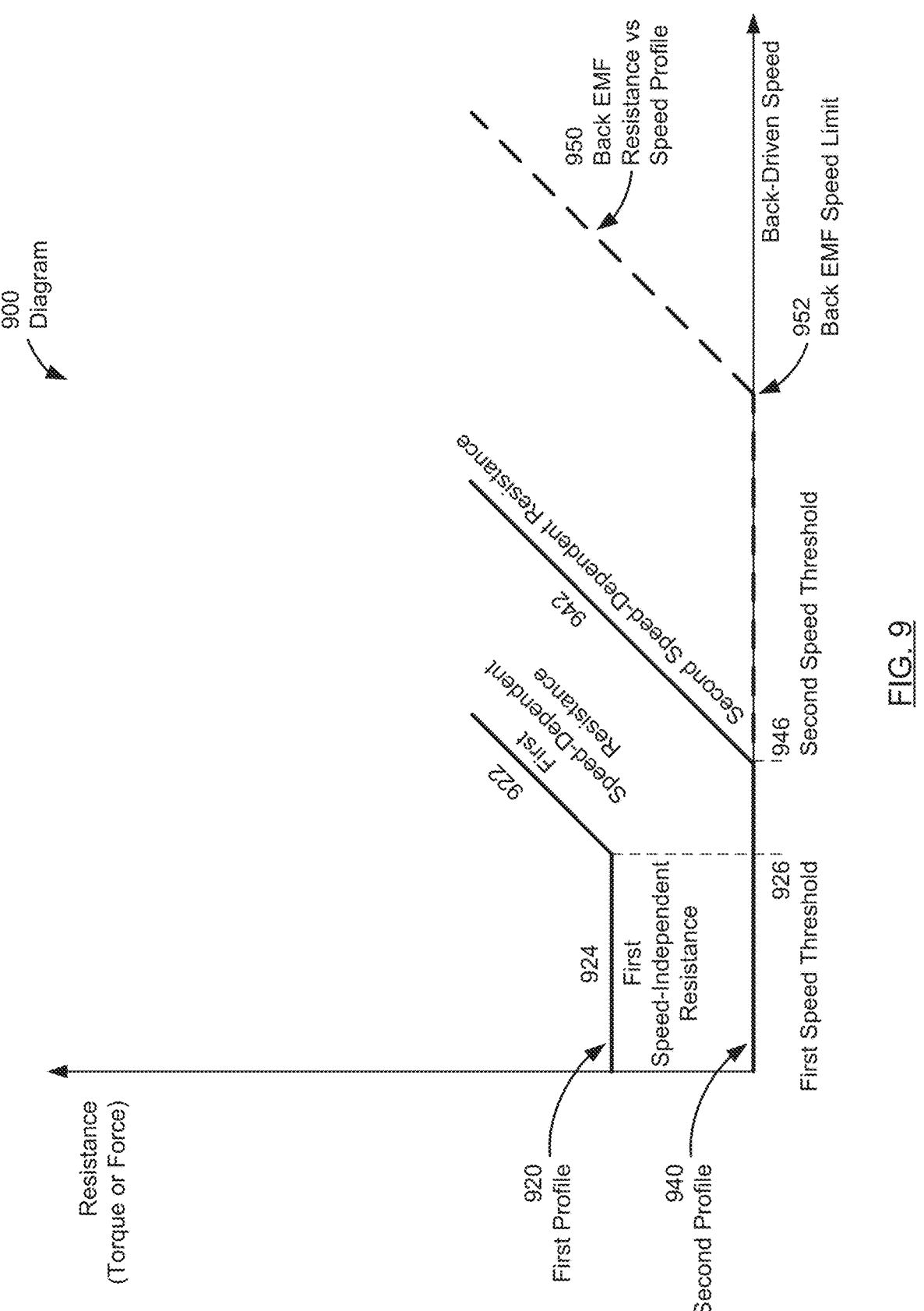
FIG. 9 shows a resistance vs. speed profile diagram, in accordance with one or more embodiments.

Referring to FIG. 9, a diagram (900) in accordance with one or more embodiments, is shown depicting resistance vs speed profiles for different control modes when already position-saturated. The diagram (900) includes a first profile (920) which may be associated with the previously described first control mode of FIG. 8. In the example shown in FIG. 9, the first profile (920) comprises a section at or below a first speed threshold (926) with a first speed-independent resistance (924), a section at or above the first speed threshold (926) with a first speed-dependent resistance (922). Referring to the discussion of the slip-lock control mode in reference to FIG. 7B, the first speed-independent resistance (924) is a result of the deviation of the actual joint position from the commanded joint position exceeding the defined threshold, causing the actuator mechanism to produce a saturated output force/torque corresponding to the first speed-independent resistance (924). The diagram (900) further includes a second profile (940) which may be associated with the previously described second control mode of FIG. 8. In the example shown in FIG. 9, the second profile (940) includes a section above the second speed threshold (946) with a second speed-dependent resistance (942). While not shown, the second profile (940) may include a second speed-independent resistance at or below the second speed threshold (946). The second speed-independent resistance may be lower than the first speed-independent resistance (924). The diagram (900) shows an immediate transition to the first speed-dependent resistance (922) upon exceeding the first speed threshold (926), and an immediate transition to the second speed-dependent resistance (942) upon exceeding the second speed threshold (946). Smooth transitions may be implemented instead, without departing from the disclosure. The exact transition between speed-independent and speed-dependent resistance may be implemented in different ways without departing from this disclosure, including transitions where the resistance supplied by the manipulator is continuous versus velocity. The first profile is distinct from, and does not intersect or overlap, the second profile for all non-zero speeds of backdriving, below the back electromotive force speed limit (952). In the example shown in FIG. 9, the slope of the first speed-dependent resistance (922) is equal to or larger than the slope of the second speed-dependent resistance (942), and the first and second profiles (920, 940) do not intersect at any point. It is understood that other slopes and/or nonlinear sections that also do not intersect can be used in other examples. Therefore, a haptic distinction of a backdriving in the first control mode from a backdriving in the second control mode is provided at any backdriven speed, until the resulting resistance reaches a level that the actuator cannot exceed (e.g., based on a maximum current for an actuator).

Referring to the manipulator assemblies described in FIGS. 1A, 1B, 2, 3, 4A, 4B, 5, and 6, the described methods may facilitate and/or improve the use of and interaction with robotic systems.

In one embodiment, the methods may be used to haptically distinguish two or more control modes. Such a haptic distinction may be useful to provide feedback that does not require the user's visual or aural attention. In such a scenario, the user may be able to detect a change in control modes, distinguish between control modes, or determine the current control mode merely based on the haptic distinction of the control modes.

In one specific example, and now referring to FIG. 6, a tool (600) has an insertion axis (612). The tool (600) may move along the insertion axis in at least two different scenarios. In a first scenario, the tool (600) moves along the insertion axis (612) as part of the operation of the tool to perform work at a target site. For example, an insertion movement along the insertion axis (612) may be performed to approach the target site with the end effector (640) of the tool (600), or a retraction movement along the insertion axis (612) may be performed to withdraw the end effector (640) from the site. In a second scenario, the tool moves along the insertion axis as part of a tool replacement procedure (e.g., when the tool is removed and replaced by another tool). Although in both the first and the second scenario, the movement of the tool (600) is along the insertion axis (612), the context in which the movement occurs is different. Different control modes may be used for the two scenarios.

For the first scenario, during the operation of the tool, the first control mode, as described in the flowchart of FIG. 8, may be used. In the first control mode, the movement of the tool along the insertion axis may be commanded (e.g., by teleoperation), while allowing a backdriving of the tool, e.g., by a user pushing or pulling the tool along the insertion axis. Depending on the backdriven speed, the user may experience a speed-independent resistance opposing the back driving, or a speed-dependent resistance opposing the back-driving.

For the second scenario, during the replacement of the tool, the second control mode, as described in the flowchart of FIG. 8, may be used. In the second control mode, a movement of the tool is not commanded, and the user may freely (with no or a minimal resistance) backdrive the tool along the insertion axis to perform the removal and/or reinsertion of the tool.

The use of distinct resistance vs. speed profiles, e.g., as shown in FIG. 9 provides haptic feedback that helps the user to distinguish or identify the current control mode of the tool being moved along the insertion axis. Specifically, at lower backdriven speeds, the user may notice the first speed-independent resistance when in the first control mode (tool operation mode in this example). In contrast, at similar speeds, no or every little resistance is provided to the user when in the second control mode (tool replacement mode in this example). At backdriven speeds beyond the first speed threshold, the user may further notice the higher first speed-dependent resistance experienced when in the first control mode (tool operation mode in this example), which is higher than the resistance that would be experienced by the user at the same speed in the second control mode (tool replacement mode in this example). At even higher backdriven speeds, the user may notice a back EMF resistance when in the second control mode. If the first control mode is implemented without the speed dependent resistance, the user would also experience the back EMF resistance at higher backdriven speeds in the first control mode because the back EMF resistance is higher than the first speed-independent resistance. However, due to the addition of the first speed-dependent resistance, as discussed in reference to FIG. 9, the first and the second control modes are haptically distinguishable at any backdriven speed.

While the invention has been described with respect to a limited number of embodiments, those skilled in the art, having benefit of this disclosure, will appreciate that other embodiments may be devised which do not depart from the scope of the invention as disclosed herein. Accordingly, the scope of the invention should be limited only by the attached claims.

What is claimed is:

1. A computer-assisted system comprising:
a manipulator arm comprising a joint, and an actuator mechanism configured to drive the joint; and
a controller comprising a computer processor, the controller communicatively coupled to the manipulator arm and configured with a first control mode and a second control mode,
wherein, in each of the first control mode and the second control mode, the controller commands the actuator mechanism to allow an external articulation to reconfigure the manipulator arm by backdriving the joint,
wherein the first control mode is distinguished from the second control mode at least by the controller being configured to, in the first control mode, command the actuator mechanism to provide a first speed-dependent resistance independent from a position of the joint in response to the joint being backdriven at a first back-driven speed above a first speed threshold, the first speed-dependent resistance opposing the joint being backdriven, and
wherein the controller, in the second control mode, is configured to command the actuator mechanism to provide a second speed-dependent resistance different from the first speed-dependent resistance in response to the joint being backdriven at a second backdriven speed above a second speed threshold.

2. The computer-assisted system of claim 1, wherein the first speed-dependent resistance simulates a speed-dependent damping response.

3. The computer-assisted system of claim 1, wherein the controller is configured to, in the second control mode, command the actuator mechanism to float the joint.

4. The computer-assisted system of claim 1, wherein the second speed threshold is higher than the first speed threshold.

5. The computer-assisted system of claim 1,
wherein, in the first control mode, the controller commands the actuator mechanism to allow the external articulation to reconfigure the manipulator arm by performing operations comprising:
obtaining an actual state of the joint;
determining a deviation between a commanded state of the joint and the actual state;
in response to the deviation exceeding a defined threshold:
adjusting the commanded state to generate an adjusted commanded state, wherein a difference between the adjusted commanded state and the actual state is smaller than the deviation, and
applying the adjusted commanded state in commanding the actuator mechanism; and
in response to the deviation not exceeding the defined threshold:
applying the commanded state in commanding the actuator mechanism.

6. The computer-assisted system of claim 1, wherein the first speed-dependent resistance increases with an amount that the first backdriven speed exceeds the first speed threshold.

7. The computer-assisted system of claim 1,
wherein the actuator mechanism comprises an actuator with a back electromotive force speed limit at which the actuator mechanism saturates, and wherein the first speed threshold is below the back electromotive force speed limit.

8. The computer-assisted system of claim 1, wherein the actuator mechanism comprises an actuator with a back electromotive force speed limit at which the actuator mechanism saturates;

wherein the controller is configured to: in the first control mode, command the actuator mechanism to resist back-driving of the joint in accordance with a first resistance versus speed profile;

wherein the controller is further configured to: in the second control mode, command the actuator mechanism to resist backdriving of the joint in accordance with a second resistance versus speed profile; and wherein the first resistance versus speed profile is distinct from the second resistance versus speed profile for all non-zero speeds of backdriving below the back electromotive force speed limit.

9. The computer-assisted system of claim 1, wherein:

the manipulator arm is configured to support and move a tool; and the joint provides a degree of freedom to move the tool along an insertion axis into a workspace.

10. The computer-assisted system of claim 1, wherein the controller is further configured to, in the first control mode, command the actuator mechanism to provide a speed-independent resistance opposing backdriving of the joint such that the speed-independent resistance provides a haptic feedback to a user causing the backdriving, wherein the haptic feedback distinguishes the backdriving of the joint in the first control mode from the backdriving of the joint in the second control mode.

11. The computer-assisted system of claim 1, wherein the first speed-dependent resistance provides a haptic feedback to a user causing the backdriving the joint in the first control mode, wherein the haptic feedback distinguishes the back-driving of the joint in the first control mode from the backdriving of the joint in the second control mode.

12. The computer-assisted system of claim 1, wherein the controller is further configured to, in the first control mode, command the actuator mechanism to provide a speed-independent resistance opposing the backdriving in response to the joint being backdriven at a speed not exceeding the first speed threshold.

13. A method for operating a robotic system comprising a manipulator arm and a controller, the manipulator arm comprising a joint and an actuator mechanism configured to drive the joint, the controller configured with a first control mode and a second control mode, the method comprising:

when the controller is in each of the first control mode and the second control mode, the controller commanding the actuator mechanism to allow an external articulation to reconfigure the manipulator arm by backdriving the joint; and when the controller is in the first control mode, the controller commanding the actuator mechanism to provide a first speed-dependent resistance independent from a position of the joint in response to the joint being backdriven at a first backdriven speed above a first speed threshold, the first speed-dependent resistance opposing the joint being backdriven, when the controller is in the second control mode, the controller is configured to command the actuator mechanism to provide a second speed-dependent resistance in response to the joint being backdriven at a second backdriven speed above a second speed threshold, wherein the first control mode is distinguished from the second control mode at least by the first speed-dependent resistance being different from the second speed-dependent resistance.

14. The method of claim 13, wherein the first speed-dependent resistance simulates a speed-dependent damping response.

15. The method of claim 13, further comprising:

when the controller is in the second control mode, the controller commanding the actuator mechanism to float the joint.

16. The method of claim 13, wherein the second speed threshold is higher than the first speed threshold.

17. The method of claim 13, wherein the controller commanding the actuator mechanism to allow an external articulation to reconfigure the manipulator arm comprises:

the controller obtaining an actual state of the joint;

the controller determining a deviation between a commanded state of the joint and the actual state;

the controller, in response to the deviation exceeding a defined threshold:

adjusting the commanded state to generate an adjusted commanded state, wherein a difference between the adjusted commanded state and the actual state is smaller than the deviation and applying the adjusted commanded state in commanding the actuator mechanism; and the controller, in response to the deviation not exceeding the defined threshold:

applying the commanded state in commanding the actuator mechanism.

18. The method of claim 13, wherein the actuator mechanism comprises an actuator with a back electromotive force speed limit at which the actuator mechanism saturates, wherein the first speed threshold is below the back electromotive force speed limit, and wherein the method further comprises:

when the controller is in the first control mode, the controller commanding the actuator mechanism to resist backdriving of the joint in accordance with a first resistance versus speed profile;

when the controller is in the second control mode, the controller commanding the actuator mechanism to resist backdriving of the joint in accordance with a second resistance versus speed profile, wherein the first resistance versus speed profile is distinct from the second resistance versus speed profile for all non-zero speeds of backdriving below the back electromotive force speed limit.

19. The method of claim 13, further comprising:

when the controller is in the first control mode, the controller commanding the actuator mechanism to provide a speed-independent resistance opposing the back-driving in response to the joint being backdriven at a speed not exceeding the first speed threshold.

20. A non-transitory machine-readable medium comprising a plurality of machine-readable instructions executed by one or more processors associated with a computer-assisted system, the plurality of machine-readable instructions causing the one or more processors associated with a robotic system comprising a manipulator arm and a controller comprising the one or more processors, the manipulator arm comprising a joint and an actuator mechanism configured to drive the joint, the controller configured with a first control mode and a second control mode, to:

when the controller is in each of the first control mode and the second control mode, the controller commanding the actuator mechanism to allow an external articulation to reconfigure the manipulator arm by backdriving the joint; and when the controller is in the first control mode, the controller commanding the actuator mechanism to provide a first speed-dependent resistance in response to the joint being backdriven at a first backdriven speed above a first speed threshold, the first speed-dependent resistance opposing the joint being backdriven, when the controller is in the second control mode, the controller is configured to command the actuator mechanism to provide a second speed-dependent resistance in response to the joint being backdriven at a second backdriven speed above a second speed threshold, wherein the first control mode is distinguished from the second control mode at least by the first speed-dependent resistance being different from the second speed-dependent resistance.

*     *     *     *     *